(12) United States Patent
Berry et al.

(10) Patent No.: US 7,919,109 B2
(45) Date of Patent: Apr. 5, 2011

(54) STABLE NON-AQUEOUS SINGLE PHASE VISCOUS VEHICLES AND FORMULATIONS UTILIZING SUCH VEHICLES

(75) Inventors: Stephen A. Berry, Hollister, CA (US); Pamela J. Fereira, Redwood City, CA (US); Houdin Dehnad, El Granada, CA (US); Anna Muchnik, Belmont, CA (US)

(73) Assignee: Intarcia Therapeutics, Inc., Hayward, CA (US)

( * ) Notice: Subject to any disclaimer, the term of this patent is extended or adjusted under 35 U.S.C. 154(b) by 214 days.

(21) Appl. No.: 12/075,435

(22) Filed: Mar. 11, 2008

(65) Prior Publication Data
US 2008/0226689 A1 Sep. 18, 2008

Related U.S. Application Data

(63) Continuation of application No. 09/627,531, filed on Jul. 28, 2000, now abandoned, which is a continuation-in-part of application No. 09/497,422, filed on Feb. 3, 2000, now Pat. No. 7,258,869.

(60) Provisional application No. 60/119,170, filed on Feb. 8, 1999.

(51) Int. Cl.
*A61F 2/00* (2006.01)
*A61K 47/00* (2006.01)
*A61K 47/30* (2006.01)

(52) U.S. Cl. ............... 424/423; 514/772; 514/772.3; 514/784; 514/785

(58) Field of Classification Search .............. 424/423; 514/772, 772.3, 784, 785
See application file for complete search history.

(56) References Cited

U.S. PATENT DOCUMENTS

| | | | |
|---|---|---|---|
| 2,110,208 | A | 3/1938 | Eggert |
| 3,632,768 | A | 1/1972 | Bergy et al. |
| 3,869,549 | A | 3/1975 | Geller |
| 4,078,060 | A | 3/1978 | Benson et al. |
| 4,310,516 | A | 1/1982 | Chang et al. |
| 4,376,118 | A | 3/1983 | Daher et al. |
| 4,588,614 | A | 5/1986 | Lauchenauer |
| 4,594,108 | A | 6/1986 | Greminger, Jr. et al. |
| 4,734,284 | A | 3/1988 | Terada et al. |
| 4,927,687 | A | 5/1990 | Nuwayser |

(Continued)

FOREIGN PATENT DOCUMENTS

EP 0265848 9/1991

(Continued)

OTHER PUBLICATIONS

Perry, J.R., et al., U.S. Appl. No. 60/122,056, which was originally filed as U.S. Appl. No. 08/595,761 on Feb. 2, 1996, including the Filing Receipt, and the "Notice of Reassign Application Number."

(Continued)

*Primary Examiner* — Blessing M Fubara
(74) *Attorney, Agent, or Firm* — Gary R. Fabian; Barbara G. McClung

(57) ABSTRACT

This invention relates to stable non-aqueous single phase viscous vehicles and to formulations utilizing such vehicles. The formulations comprise at least one beneficial agent uniformly suspended in the vehicle. The formulation is capable of being stored at temperatures ranging from cold to body temperature for long periods of time. The formulations are capable of being uniformly delivered from drug delivery systems at an exit shear rate of between about 1 to $1 \times 10^{-7}$ reciprocal second.

20 Claims, 10 Drawing Sheets

U.S. PATENT DOCUMENTS

| | | | |
|---|---|---|---|
| 4,952,402 A | 8/1990 | Sparks et al. | |
| 5,034,229 A | 7/1991 | Magruder et al. | |
| 5,057,318 A | 10/1991 | Magruder et al. | |
| 5,071,642 A | 12/1991 | Lahr et al. | |
| 5,110,596 A | 5/1992 | Magruder et al. | |
| 5,120,712 A | 6/1992 | Habener | |
| 5,284,655 A | 2/1994 | Bogdansky et al. | |
| 5,290,271 A | 3/1994 | Jernberg | |
| 5,300,302 A | 4/1994 | Tachon et al. | |
| 5,352,662 A | 10/1994 | Brooks et al. | |
| 5,371,089 A | 12/1994 | Rattan | |
| 5,374,620 A | 12/1994 | Clark et al. | |
| 5,385,738 A | 1/1995 | Yamahira et al. | |
| 5,411,951 A | 5/1995 | Mitchell | |
| 5,424,286 A | 6/1995 | Eng | |
| 5,512,293 A | 4/1996 | Landrau et al. | |
| 5,540,912 A | 7/1996 | Roorda et al. | |
| 5,545,618 A | 8/1996 | Buckley et al. | |
| 5,571,525 A | 11/1996 | Roorda et al. | |
| 5,574,008 A | 11/1996 | Johnson et al. | |
| 5,614,221 A | 3/1997 | Fjellstrom | |
| 5,635,213 A | 6/1997 | Nystrom et al. | |
| 5,668,170 A * | 9/1997 | Gyory | 514/449 |
| 5,728,396 A | 3/1998 | Peery, Jr. et al. | |
| 5,747,058 A | 5/1998 | Tipton et al. | |
| 5,756,450 A | 5/1998 | Hahn et al. | |
| 5,782,396 A | 7/1998 | Mastri et al. | |
| 5,814,323 A | 9/1998 | Lyle | |
| 5,843,891 A | 12/1998 | Sherman | |
| 5,882,676 A * | 3/1999 | Lee et al. | 424/449 |
| 5,904,935 A | 5/1999 | Eckenhoff et al. | |
| 5,906,830 A | 5/1999 | Farinas et al. | |
| 5,928,666 A | 7/1999 | Farinas et al. | |
| 5,932,547 A | 8/1999 | Stevenson et al. | |
| 5,958,909 A | 9/1999 | Habener | |
| 5,972,370 A | 10/1999 | Eckenhoff et al. | |
| 5,972,373 A | 10/1999 | Yajima et al. | |
| 5,985,305 A | 11/1999 | Peery, Jr. et al. | |
| 5,997,527 A | 12/1999 | Gumucio et al. | |
| 6,017,545 A * | 1/2000 | Modi | 424/400 |
| 6,113,938 A | 9/2000 | Chen et al. | |
| 6,124,261 A | 9/2000 | Stevenson et al. | |
| 6,127,520 A | 10/2000 | Ueda et al. | |
| 6,130,200 A | 10/2000 | Brodbeck et al. | |
| 6,132,420 A | 10/2000 | Dionne et al. | |
| 6,156,331 A | 12/2000 | Peery, Jr. et al. | |
| 6,218,431 B1 * | 4/2001 | Schoen et al. | 514/520 |
| 6,235,712 B1 | 5/2001 | Stevenson et al. | |
| 6,261,584 B1 | 7/2001 | Peery, Jr. et al. | |
| 6,270,787 B1 | 8/2001 | Ayer | |
| 6,287,295 B1 | 9/2001 | Chen et al. | |
| 6,331,311 B1 | 12/2001 | Brodbeck et al. | |
| 6,375,978 B1 | 4/2002 | Kleiner et al. | |
| 6,395,292 B2 | 5/2002 | Peery, Jr. et al. | |
| 6,468,961 B1 | 10/2002 | Brodbeck et al. | |
| 6,508,808 B1 | 1/2003 | Carr et al. | |
| 6,524,305 B1 | 2/2003 | Peterson et al. | |
| 6,544,252 B1 | 4/2003 | Theeuwes et al. | |
| 6,635,268 B2 | 10/2003 | Peery, Jr. et al. | |
| 6,673,767 B1 | 1/2004 | Brodbeck et al. | |
| 6,939,556 B2 | 9/2005 | Lautenbach | |
| 7,014,636 B2 | 3/2006 | Gilbert | |
| 7,074,423 B2 | 7/2006 | Fereira et al. | |
| 7,163,688 B2 | 1/2007 | Peery et al. | |
| 7,207,982 B2 | 4/2007 | Dionne et al. | |
| 7,258,869 B1 | 8/2007 | Berry et al. | |
| 7,655,257 B2 | 2/2010 | Peery, Jr. et al. | |
| 2002/0034532 A1 | 3/2002 | Brodbeck et al. | |
| 2003/0044467 A1 | 3/2003 | Brodbeck et al. | |
| 2003/0211974 A1 | 11/2003 | Brodbeck et al. | |
| 2004/0224903 A1 | 11/2004 | Berry et al. | |
| 2005/0008661 A1 | 1/2005 | Fereira et al. | |
| 2005/0112188 A1 | 5/2005 | Eliaz et al. | |
| 2005/0175701 A1 | 8/2005 | Pan et al. | |
| 2005/0266087 A1 | 12/2005 | Junnarkar et al. | |
| 2005/0276856 A1 | 12/2005 | Fereira et al. | |
| 2006/0013879 A9 | 1/2006 | Brodbeck et al. | |
| 2006/0141040 A1 | 6/2006 | Chen et al. | |
| 2006/0142234 A1 | 6/2006 | Chen et al. | |
| 2006/0193918 A1 | 8/2006 | Rohloff et al. | |
| 2006/0216242 A1 | 9/2006 | Rohloff et al. | |
| 2006/0246138 A1 | 11/2006 | Rohloff et al. | |
| 2007/0027105 A1 | 2/2007 | Junnarkar et al. | |
| 2007/0281024 A1 | 12/2007 | Lautenbach et al. | |

FOREIGN PATENT DOCUMENTS

| | | |
|---|---|---|
| EP | 0379147 B1 | 9/1994 |
| GB | 1049104 | 11/1966 |
| WO | 95/34285 | 12/1995 |
| WO | 96/39142 | 12/1996 |
| WO | 96/40049 | 12/1996 |
| WO | 97/28181 | 8/1997 |
| WO | 98/00152 | 1/1998 |
| WO | 98/00157 | 1/1998 |
| WO | 98/00158 | 1/1998 |
| WO | 98/16250 | 4/1998 |
| WO | 98/27960 | 7/1998 |
| WO | 98/27962 | 7/1998 |
| WO | 98/27963 | 7/1998 |

OTHER PUBLICATIONS

Bell et al, "Impact of Moisture on Thermally Induced . . . ," Drug Deliv. Res. & Dev., John Wiley & Sons, Inc. (U.S.A.), p. S4-S26, 1995.

Bertoncello et al., "Haematopoietic radioprotection by Cremophor EL: a polyethoxylated castor oil," Int J Radiat Biol, vol. 67 (No. 1), p. 57-64, 1995.

Cas RN 56-81-5, Nov. 16, 1984.

Chang et al, "Biodegradeable Polyester Implants . . . ," Pharm. Tech., p. 80-84, 1996.

Desai et al., "Protein Structure in the Lyophilized . . . " J. Amer. Chem. Soc., p. 9420-9422, 1994.

Hageman, Michael J., "The Role of Moisture in Protein Stability," Drug Dev. & Ind. Pharm., vol. 14 (No. 14), p. 2047-2070, 1988.

Hisatomi et al., "Toxicity of polyoxyethylene hydrogenated castor oil 60 (HCO-60) in experimental animals," J Toxicol Sci, Aug. 1993: 18 Supp 3:1-9.

Introduction to Antibodies downloaded from the world wide web on May 2, 2007; http://www.chemicon.com/resource/ANT101/a1.asp.

Knepp et al, "Identification of antioxidants for prevention of peroxide-mediated oxidation of recombinant human ciliary neurotrophic factor and recombinant human nerve growth factor," J. Pharm. Sci. Tech., p. 163-171. vol. 50, No. 3, 1996.

Knepp et al, "Stability of Nonaqueous Suspension . . . ," Pharm. Res., vol. 15 (No. 7), p. 1090-1095, 1998.

Manning et al, "Stability of Protein . . . ," Pharm. Res., vol. 6 (No. 11), p. 903-918, 1989.

Roman et al., "Cholestasis in the rat by means of intravenous administration of cyclosporine vehicle, Cremophor EL," Transplantation, Oct. 1989, 48(4), p. 554-8.

Wang et al, "Parenteral Formulations . . . ," J. Parenteral Sci. Tech., p. S4-S26, 1988.

Yu et al, "Preparation, Characterization, and . . . ," J. Pharm. Sci., vol. 85 (No. 4), p. 396-401, 1996.

Zhang et al, "A New Strategy . . . ," Pharm Res., vol. 12 (No. 10), p. 1447-1452, 1995.

* cited by examiner

STABLE NON-AQUEOUS SINGLE PHASE VISCOUS VEHICLES AND FORMULATIONS UTILIZING SUCH VEHICLES

CROSS-REFERENCE TO RELATED APPLICATIONS

This application is a Continuation of U.S. patent application Ser. No. 09/627,531, filed 28 Jul. 2000, now abandoned, which is a Continuation-in-Part of 09/497,422, filed 3 Feb. 2000, now U.S. Pat. No. 7,258,869, which claims the benefit of U.S. Provisional Application Ser. No. 60/119,170, filed 8 Feb. 1999, now expired, all of which applications are herein incorporated by reference in their entireties in the present application.

FIELD OF THE INVENTION

This invention relates to stable non-aqueous single phase biocompatible viscous vehicles capable of suspending beneficial agents and uniformly dispensing said agents at low flow rates and more particularly to stable uniformly mixed formulations of beneficial agents in stable non-aqueous single phase biocompatible viscous vehicles.

REFERENCES

The following references are referred to by numbers in brackets ([ ]) at the relevant portion of the specification.
1. Wang, et al., *J. Parenteral Sci. Tech*, 42: S4-S26 (1988).
2. Desai, et al., *J. Am. Chem. Soc.*, 116: 9420-9422 (1994).
3. Chang, et al., *Pharm. Tech.*, 80-84 (Jan. 1996).
4. Manning, et al., *Pharm. Res.*, 6: 903-918 (1989).
5. Hageman, *Drug Dev. Ind. Pharm*, 14: 2047-2070 (1988).
6. Bell, et al., *Biopolymers*, 35: 201-209 (1995).
7. Zhang, et al., *Pharm. Res.* 12: 1447-1452 (1995).
8. PCT published application 98/00158
9. PCT published application 98/16250
10. Knepp, et al., *Pharm. Res.* 15 (7) 1090-1095 (1998).
11. PCT published application 98/00157
12. PCT published application 98/00152
13. U.S. Pat. No. 5,540,912
17. Yu, et al., *J. Pharm. Sci.*, 85: 396-401 (1996).
18. Mitchell, U.S. Pat. No. 5,411,951 (1995).
19. Brooks, et al., U.S. Pat. No. 5,352,662 (1994)
20. Geller, L., U.S. Pat. No. 3,869,549 (1975).
21. Larsen, et al., PCT Publication No. WO95/34285 (1995).
22. Knepp, et al., *J. Pharm. Sci. Tech*, 50: 163-171 (1996).
23. U.S. Pat. No. 5,614,221
24. U.S. Pat. No. 4,594,108
25. U.S. Pat. No. 5,300,302
26. U.S. Pat. No. 4,588,614
27. U.S. Pat. No. 4,310,516
28. U.S. Pat. No. 5,635,213
29. EP 379,147

BACKGROUND OF THE INVENTION

Peptides, polypeptides, proteins and other proteinaceous substances (e.g., viruses, antibodies) collectively referred to herein as proteins, have great utility as pharmaceuticals in the prevention, treatment and diagnosis of disease. Proteins are naturally active in aqueous environments, thus the preferred formulations of proteins have been in aqueous solutions. However, proteins are only marginally stable in aqueous solutions. Thus, protein pharmaceuticals often have short shelf-lives under ambient conditions or require refrigeration. Further, many proteins have only limited solubility in aqueous solutions. Even when they are soluble at high concentrations, they are prone to aggregation and precipitation.

Because proteins can easily degrade, the standard method for delivering such compounds has been daily injections. Proteins can degrade via a number of mechanisms, including deamidations of asparagine and glutamine; oxidation of methionine and, to a lesser degree, tryptophan, tyrosine and histidine; hydrolysis of peptide bonds; disulfide interchange; and racemization of chiral amino acid residues [1-7]. Water is a reactant in nearly all of these degradation pathways. Further, water acts as a plasticizer, which facilitates unfolding and irreversible aggregation of proteins. Since water is a participant in almost all protein degradation pathways, reduction of aqueous protein solution to a dry powder provides an alternative formulation methodology to enhance the stability of protein pharmaceuticals.

One approach to stabilizing proteins is to dry them using various techniques, including freeze-drying, spray-drying, lyophilization, and desiccation. Dried proteins are stored as dry powders until their use is required.

A serious drawback to drying of proteins is that often one would like to use proteins in some sort of flowable form. Parenteral injection and the use of drug delivery devices for sustained delivery of drug are two examples of the applications where one would like to use proteins in a flowable form. For injection, dried proteins must be reconstituted, adding additional steps which are time-consuming and where contamination may occur, and exposing the protein to potentially destabilizing conditions [7]. For drug delivery devices the protein formulations must be stable for extended periods of time at body temperature and maintain their flowability for the expected life of the device.

Solution formulations of proteins/peptides in non-aqueous polar aprotic solvents such as DMSO and DMF have been shown to be stable at elevated temperatures for long periods of time [8]. However, such solvent based formulations will not be useable for all proteins since many proteins have low solubility in these solvents. The lower the solubility of the protein in the formulation, the more solvent would have to be used for delivery of a specific amount of protein. Low concentration solutions may be useful for injections, but may not be useful for long term delivery at low flow rates.

Proteins have been formulated for delivery using perfluorodecalin [9, 10], methoxyflurane [9], high concentrations in water [11], polyethylene glycol [12], PLGA [13, 14], ethylenevinylacetate/polyvinylpyrridone mixtures [15], PEG400/povidone [16]. However, these formulations were not shown to retain a uniform suspension of protein in viscous vehicle over long periods of time.

Many biologically active compounds degrade over time in aqueous solution. Carriers in which proteins do not dissolve but rather are suspended, can often offer improved chemical stability. Furthermore, it can be beneficial to suspend the beneficial agent in a carrier when the agent exhibits low solubility in the desired vehicle. However, suspensions can have poor physical stability due to settling and agglomeration of the suspended beneficial agent. The problems with non-aqueous carriers tend to be exacerbated as the concentration of the active compound is increased.

Dispersing powdered proteins or peptides in lipid vehicles to yield parenteral sustained release formulations has been investigated [17-21]. The vehicles used were either various vegetable (sesame, soy, peanut, etc.) or synthetic oils (e.g., Miglyol) gelled with aluminum fatty acid esters such as aluminum stearates (mono-, di- or tri-), or with a polyglycerol ester. Although theoretically these vehicles might preclude solution denaturation and protect the drug from aqueous chemical degradation, the vehicles themselves are unstable at higher temperatures. The storage of liquid vegetable oils at body temperatures results in the formation of reactive species such as free fatty acids and peroxides (a process which is accelerated by the presence of traces of various metal ions such as copper or iron which can leach from some implantable devices). These peroxides not only adversely affect protein stability [22] but would be toxic when delivered directly to, for example, the central nervous system of a human or animal.

The sustained delivery of drugs has many advantages. Use of implantable devices assures patient compliance, since the delivery device is tamper-proof. With one insertion of a device, rather than daily injections, there is reduced site irritation, fewer occupational hazards for practitioners improved cost effectiveness through decreased costs of equipment for repeated injections, reduced hazards of waste disposal, and enhanced efficacy through controlled release as compared with depot injection. The use of implantable devices for sustained delivery of a wide variety of drugs or other beneficial agents is well known in the art. Typical devices are described, for example, in U.S. Pat. Nos. 5,034,229; 5,057,318; 5,110,596; and 5,782,396. The disclosure of each of these patents is incorporated herein by reference.

For drug delivering implants, dosing durations of up to one year are not unusual. Beneficial agents which have low therapeutic delivery rates are prime candidates for use in implants. When the device is implanted or stored, settling of the beneficial agent in a liquid formulation can occur. This heterogeneity can adversely affect the concentration of the beneficial agent dispensed. Compounding this problem is the size of the implanted beneficial agent reservoir. Implant reservoirs are generally on the order of 25-250 μl, but can be up to 25 ml.

Viscous formulations have been prepared using two separate components to be mixed with drug at use [23], thickening agents added to aqueous compositions [24], gelling agents added to aqueous drug solutions [25], porous textile sheet material [26], thickening agents with oleaginous material [27], viscous aqueous carrier for limited solubility drug [28], and extrudable elastic gels [29]. However, these formulations are mixed at use, contain aqueous components, use sheet matrices, or are delivered topically, orally, or intraduodenally.

Stability of formulations can be enhanced by freeze-drying, lyophilizing or spray-drying the active ingredient. The process of drying the active ingredient includes further advantages such as compounds which are relatively unstable in aqueous solution can be processed and filled into dosage containers, dried without elevated temperatures, and then stored in the dry state in which there are relatively few stability problems.

Pharmaceutical formulations, particularly parenteral products, should be sterilized after being sealed in the final container and within as short a time as possible after the filling and sealing have been completed. (See, for example Remington, Pharmaceutical Sciences, 15$^{th}$ ed. (1975)). Examples of sterilization techniques include thermal or dry-heat, aseptic, and ionized radiation. Combinations of these sterilization procedures may also be used to produce a sterile product.

There is a need to be able to deliver protein compositions to the body which are stable at body temperatures over extended periods of time to enable long term delivery of the protein. There is a need to be able to deliver concentrations of proteins that are efficacious. There is a need for a novel non-aqueous formulation capable of homogeneously suspending proteins and dispensing such agents at body temperatures and low flow rates over extended periods of time.

SUMMARY OF THE INVENTION

The present invention provides stable single phase non-aqueous biocompatible viscous vehicles capable of forming uniform suspensions with proteins. The components of the viscous vehicle comprise at least two of polymer, surfactant, and solvent. The ratios of the components will vary depending on the molecular weight of the components and the desired viscosity of the final vehicle. Presently preferred component ratios are: polymer, about 5% to about 60%; solvent, about 5% to about 60%; and surfactant, about 5% to about 40%.

The present invention also provides stable formulations in which beneficial agents are uniformly suspended in stable single phase non-aqueous biocompatible viscous vehicles. In particular, the beneficial agents are formulated in the viscous vehicles at concentrations of at least about 0.1%, depending upon the potency of the beneficial agent. These stable formulations may be stored at the temperature appropriate for the beneficial agent, ranging from cold, to body temperature (about 37° C.) for long periods of time (1 month to 1 year or more). In a preferred embodiment the formulation comprises about 0.1 to 50% (w/w) of beneficial agent, depending on the potency of the beneficial agent, the duration of treatment, and the rate of release for the drug delivery system.

These formulations are especially useful in implantable delivery devices for long term delivery (e.g., 1 to 12 months or longer) of beneficial agent at body temperature, preferably about 37° C. Thus, the present invention also provides for the delivery of said proteins to the body over extended period of time to enable long term delivery of the protein at low flow rates of about 0.3 to 100 μl/day, preferably about 0.3 to 4 μl/day for about a 6 month delivery period and preferably 5 to 8 μl/day for about a 3 month delivery period.

In another aspect, the invention provides methods for preparing stable non-aqueous biocompatible formulations of a beneficial agent in a single phase viscous vehicle. Preferred formulations comprise about 0.1 to 50% (w/w) beneficial agent depending on the potency of the beneficial agent, the duration of treatment, and the rate of release from the delivery system.

In yet a further aspect, the invention provides methods for treating a subject suffering from a condition which may be alleviated by administration of a beneficial agent, said methods comprising administering to said subject an effective amount of a stable non-aqueous formulation comprising at least one beneficial agent uniformly suspended in a single phase viscous vehicle.

A further aspect of the invention is that non-aqueous single phase viscous vehicles containing beneficial agents are chemically and physically stable over a broad temperature range for long periods of time. The beneficial agents in the viscous vehicles are also chemically and physically stable over a broad temperature range for long periods of time. Thus, these formulations are advantageous in that they may be shipped and stored at temperatures below, at, or above room temperature for long period of time. They are also suitable for use in implantable delivery devices in which the formulation must be stable at body temperature for extended periods of time.

The formulations of the present invention also remain stable when delivered from implantable drug delivery systems. The beneficial agents have been shown to exhibit zero order release rates when delivered from implantable drug delivery systems at very low flow rates over extended periods of time.

DETAILED DESCRIPTION OF THE INVENTION

Figure 1:
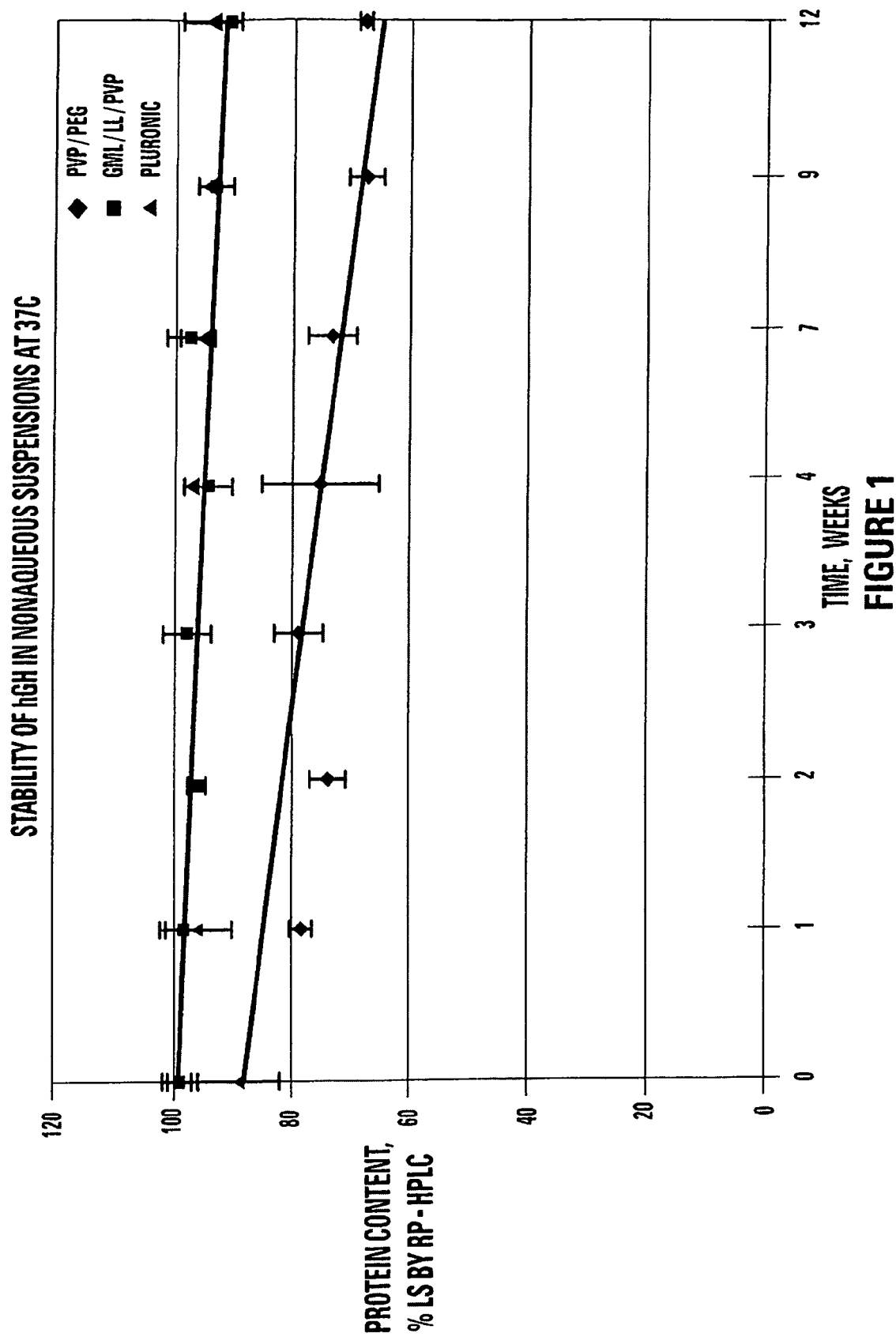
FIG. 1 shows the stability of hGH formulations of the present invention as determined at 37° C. by reverse phase HPLC.

The present invention is drawn to the unexpected discovery that uniformly suspending beneficial agents in non-aqueous single phase biocompatible viscous vehicles results in stable formulations which can be delivered at body temperature over an extended period of time at low flow rates. Previously known formulations of beneficial agents which are buffered aqueous or non-aqueous solutions which may or may not contain excipients do not provide formulations which can be uniformly dispensed at body temperatures at low flow rates over an extended period of time without exhibiting unacceptable amounts of aggregation or degradation of the formulation. The presently claimed formulations stabilize beneficial agents and can be stored at the temperature appropriate for the beneficial agent. The temperatures can range from cold (not exceeding 8° C.) to body temperature (about 37° C.) for long periods of time. These formulations are especially useful in implantable delivery devices for long term delivery (e.g., 1 to 12 months or longer) of drug at low flow rates and at body temperature, preferably about 37° C.

Standard beneficial agent formulations consist of dilute aqueous or non-aqueous solutions or suspensions. Drug stability is usually achieved by varying one or more of the following: pH, buffer type, ionic strength, excipients (EDTA, ascorbic acid, etc.) For these formulations, degradation pathways requiring water (hydrolysis, deamidation, racemization) cannot be fully stabilized. In the present invention, beneficial agents formulated in non-aqueous biocompatible single phase viscous vehicles containing for example, polyvinylpyrrolidone, vinyl acetate, and/or polyoxyethylenepolyoxypropylene block copolymers were shown to be chemically and physically stable. The viscosity of the formulation will depend upon a number of criteria, including the beneficial agent potency and concentration, and the process by which the formulation is prepared. The viscosity of the formulation can be chosen so that the desired amount of beneficial agent is delivered over the desired period of time.

The invention also consists of non-aqueous single phase biocompatible viscous vehicles capable of uniformly suspending beneficial agents and formulations containing at least one beneficial agent uniformly suspended in said viscous vehicle. The invention also consists of formulations containing at least one beneficial agent uniformly suspended in a non-aqueous single phase biocompatible viscous vehicle, which formulations are stable for an extended period of time at body temperatures, and capable of delivering said beneficial agents uniformly at low flow rates. The discovery consists of the realization that stable non-aqueous viscous vehicles improve the stability of beneficial agents in a wide range of formulation conditions including concentration, elevated temperatures and duration of stable formulation, thus making possible the delivery of beneficial agents in long term implantable devices that would not otherwise be feasible.

DEFINITIONS

As used herein, the following terms have the following meanings:

The term "chemical stability" means that an acceptable percentage of degradation products produced by chemical pathways such as oxidation, deamidation, or hydrolysis is formed. In particular, a formulation is considered chemically stable if no more than about 35% breakdown products are formed after 2 months at 37° C.

The term "physical stability" means that an acceptable percentage of aggregates (e.g., dimers, trimers and larger forms) are formed by the beneficial agent. For the formulation (viscous vehicle and beneficial agent) this term means that the formulation retains stability, flowability, and the ability to uniformly dispense the beneficial agent. In particular, a formulation is considered physically stable if no more than about 15% aggregates are formed after two months at 37° C.

The term "stable formulation" means that at least about 65% chemically and physically stable beneficial agent remains after two months at 37° C. (or equivalent conditions at an elevated temperature). Particularly preferred formulations are those which retain at least about 80% chemically and physically stable beneficial agent under these conditions. Especially preferred stable formulations are those which do not exhibit degradation after sterilizing irradiation (e.g., gamma, beta or electron beam).

The term "beneficial agent" means peptides, proteins, nucleotides, hormones, viruses, antibodies, etc. that comprise polymers of amino acid or nucleic acid residues. These beneficial agents are generally degradable in water and generally stable as a dry powder at elevated temperatures. Synthetically produced, naturally derived or recombinantly produced moieties are included in this term. The term also includes lipoproteins and post translationally modified forms, e.g., glycosylated proteins. Analogs, derivatives, agonists, antagonists and pharmaceutically acceptable salts of any of these are included in this term. The term also includes proteins and/or protein substances which have D-amino acids, modified, derivatized or non-naturally occurring amino acids in the D- or L-configuration and/or peptomimetic units as part of their structure. The term protein will be used in the present invention. The term also means that the beneficial agent is present in the solid state, e.g., powder or crystalline.

The term "excipient" means a more or less inert substance in a formulation that is added as a diluent or vehicle or to give form or consistency. Excipients are distinguished from solvents such as ETOH, which are used to dissolve drugs in formulations. Excipients include non-ionic surfactants such as polysorbates, which are used to solubilize drugs in formulations; preservatives such as benzyl alcohols or methyl or propyl parabens, which are used to prevent or inhibit microbial growth; chelating agents; flavoring agents; and other pharmaceutically acceptable formulation aides.

The term "viscous vehicle" means a vehicle with a viscosity in the range of about 1,000 to 10,000,000 poise. The term includes Newtonian and non-Newtonian materials. Preferred are vehicles with a viscosity of about 10,000 to 250,000 poise. The formulations of this invention can uniformly expel beneficial agents suspended in the viscous vehicle from implantable drug delivery devices. The formulations exhibit a shear rate at the exit of said devices of 1 to $1 \times 10^{-7}$ reciprocal second, preferably an exit shear rate of $1 \times 10^{-2}$ to $1 \times 10^{-5}$ reciprocal second.

The term "single phase" means a solid, semi-solid, or liquid homogeneous system that is both physically and chemically uniform throughout as determined by differential scanning calorimetry (DSC). The DSC scan should show one peak indicative of a single phase.

The term "biocompatible" means a property or characteristic of a viscous vehicle to disintegrate or break down, over a prolonged period of time, in response to the biological environment in the patient, by one or more physical or chemical degradative processes, for example by enzymatic action, oxidation or reduction, hydrolysis (proteolysis), displacement, e.g. ion exchange, or dissolution by solubilization, emulsion or micelle formation, and which material is then absorbed by the body and surrounding tissue, or otherwise dissipated thereby.

The term "polymer" includes polyesters such as PLA (polylactic acid) [having an inherent viscosity in the range of about 0.5 to 2.0 i.v.] and PLGA (polylacticpolyglycolic acid) [having an inherent viscosity in the range of about 0.5 to 2.0 i.v.], pyrrolidones such as polyvinylpyrrolidone (having a molecular weight range of about 2,000 to 1,000,000), esters or ethers of unsaturated alcohols such as vinyl acetate, and polyoxyethylenepolyoxypropylene block copolymers (exhibiting a high viscosity at 37° C.) such as Pluronic 105. Currently preferred polymer is polyvinylpyrrolidone.

The term "solvent" includes carboxylic acid esters such as lauryl lactate, polyhydric alcohols such as glycerin, polymers of polyhydric alcohols such as polyethylene glycol (having a molecular weight of about 200 to 600), fatty acids such as oleic acid and octanoic acid, oils such as castor oil, propylene carbonate, lauryl alcohol, or esters of polyhydric alcohols such as triacetin acetate. Currently preferred is lauryl lactate.

The term "surfactant" includes esters of polyhydric alcohols such as glycerol monolaurate, ethoxylated castor oil, polysorbates (for example Polysorbate 80), esters or ethers of saturated alcohols such as myristyl lactate (Ceraphyl 50), and polyoxyethylenepolyoxypropylene block copolymers such as Pluronic (for example, F68). Currently preferred are gylcerol monolaurate and polysorbates.

The term "antioxidant" means a pharmaceutically acceptable aid for stablization of the beneficial agent against degradation such as oxidation. Antioxidants include, but are not limited to, tocopherol (vitamin E), ascorbic acid, ascorbyl palmitate, butylated hydroxyanisole, butylated hydroxytoluene, and propyl gallate. A preferred antioxidant depends on solubility and the efficiency of the antioxidant for protecting against degradation or chemical change of the beneficial agent in the preferred vehicle. Currently preferred is ascorbyl palmitate.

Preparation of Formulations

The present invention is drawn to stable non-aqueous single phase biocompatible viscous vehicles capable of suspending beneficial agents and uniformly dispensing said beneficial agents at body temperatures at low flow rates over an extended period of time. The present invention is also directed to formulations containing beneficial agents uniformly suspended in said single phase biocompatible viscous vehicles which are stable for prolonged periods of time at body temperatures.

Examples of beneficial agents that may be formulated using the present invention include those peptides or proteins that have biological activity or that may be used to treat a disease or other pathological condition. They include, but are not limited to, adrenocorticotropic hormone, angiotensin I and II, atrial natriuretic peptide, bombesin, bradykinin, calcitonin, cerebellin, dynorphin N, alpha and beta endorphin, endothelin, enkephalin, epidermal growth factor, fertirelin, follicular gonadotropin releasing peptide, galanin, glucagon, glucagon-like peptide-1 (GLP-1), gonadorelin, gonadotropin, goserelin, growth hormone releasing peptide, histrelin, human growth hormone, insulin, interferons, leuprolide, LHRH, motilin, nafarerlin, neurotensin, oxytocin, relaxin, somatostatin, substance P, tumor necrosis factor, triptorelin, vasopressin, growth hormone, nerve growth factor, blood clotting factors, ribozymes, and antisense oligonucleotides. Analogs, derivatives, antagonists agonists and pharmaceutically acceptable salts of the above may also be used.

The beneficial agents useful in the formulations and methods of the present invention can be used in the form of a salt, preferably a pharmaceutically acceptable salt. Useful salts are known to those of skill in the art and include salts with inorganic acids, organic acids, inorganic bases, or organic bases.

Beneficial agents that are not readily soluble in non-aqueous solvents are preferred for use in the present invention. One of skill in the art can easily determine which compounds will be useful on the basis of their solubility. The amount of beneficial agent may vary depending on the potency of the compound, the condition to be treated, the solubility of the compound, the expected dose and the duration of administration. (See, for example, Gilman, et. al, The Pharmacological Basis of Therapeutics, $7^{th}$ ed. (1990) and Remington, Pharmacological Sciences, $18^{th}$ ed. (1990), the disclosures of which are incorporated herein by reference.)

Figure 2:
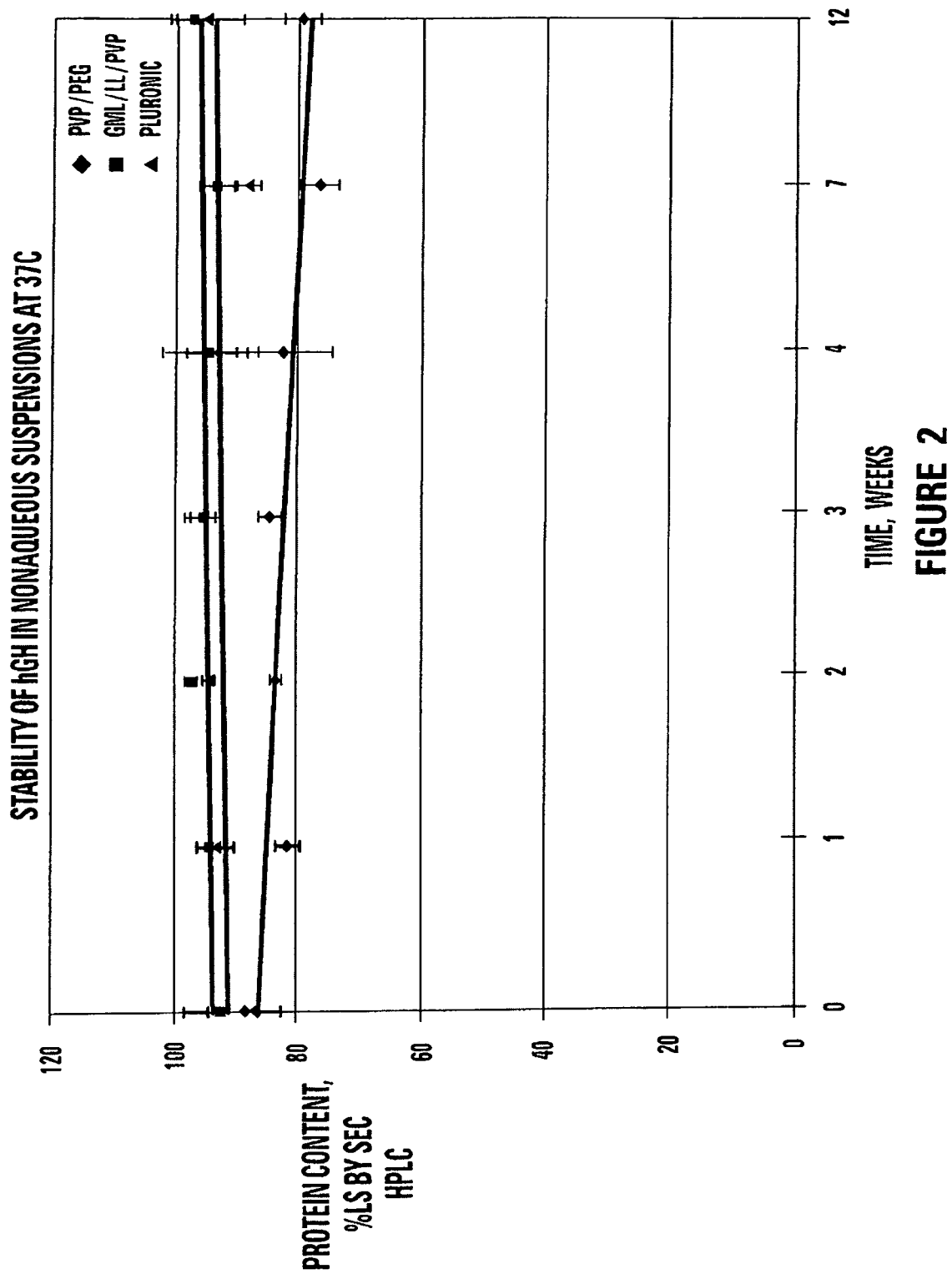
FIG. 2 shows the stability of hGH formulations of the present invention as determined at 37° C. by size exclusion chromatography.
Figure 3:
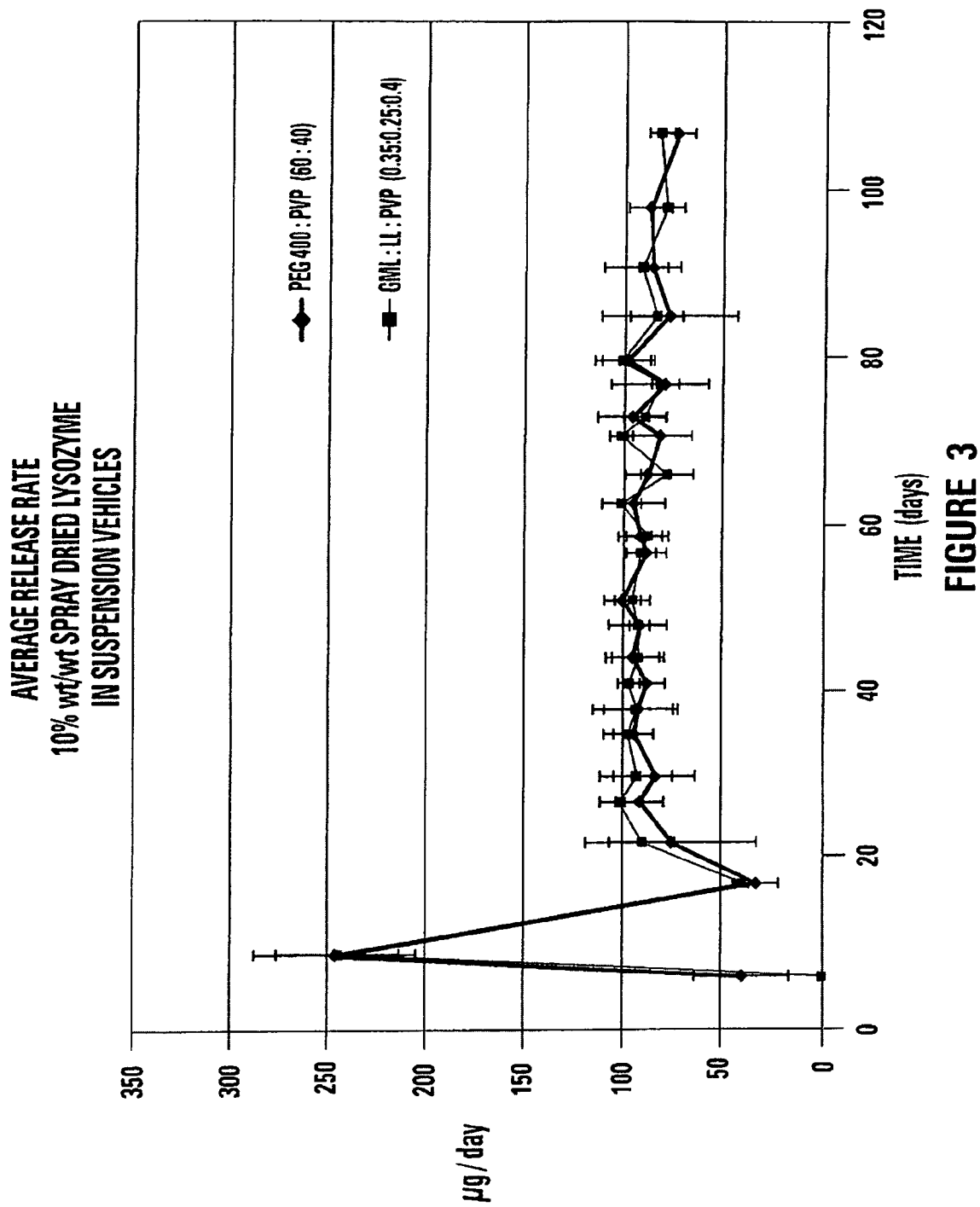
FIG. 3 shows the average release rate (μl/day) of 10% (w/w) spray-dried lysozyme in formulations of the present invention.
Figure 4:
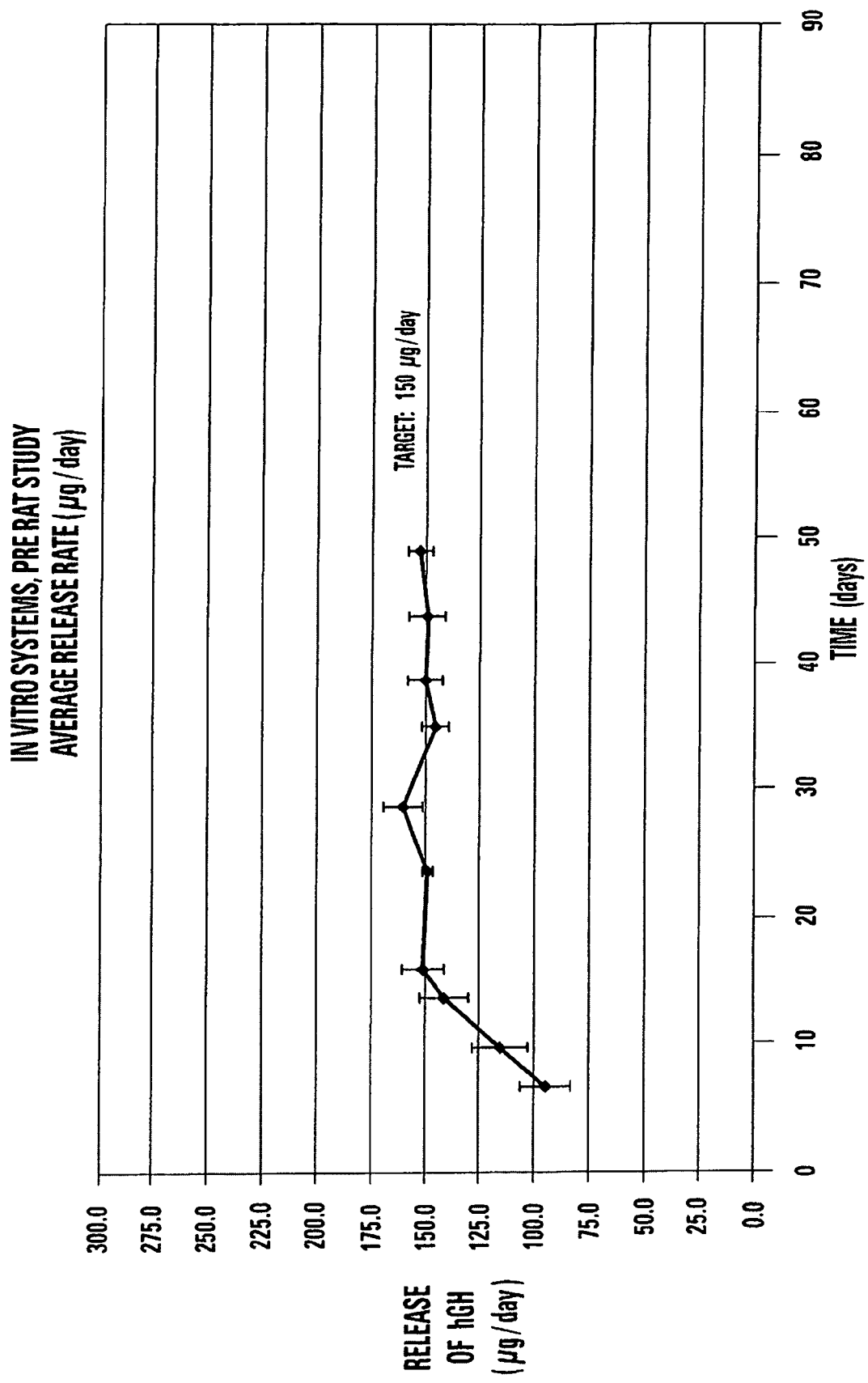
FIG. 4 shows the average release rate (μl/day) of 10% (w/w) spray-dried hGH in a glycerol monolaurate/lauryl lactate/polyvinylpyrrolidone vehicle.
Figure 5:
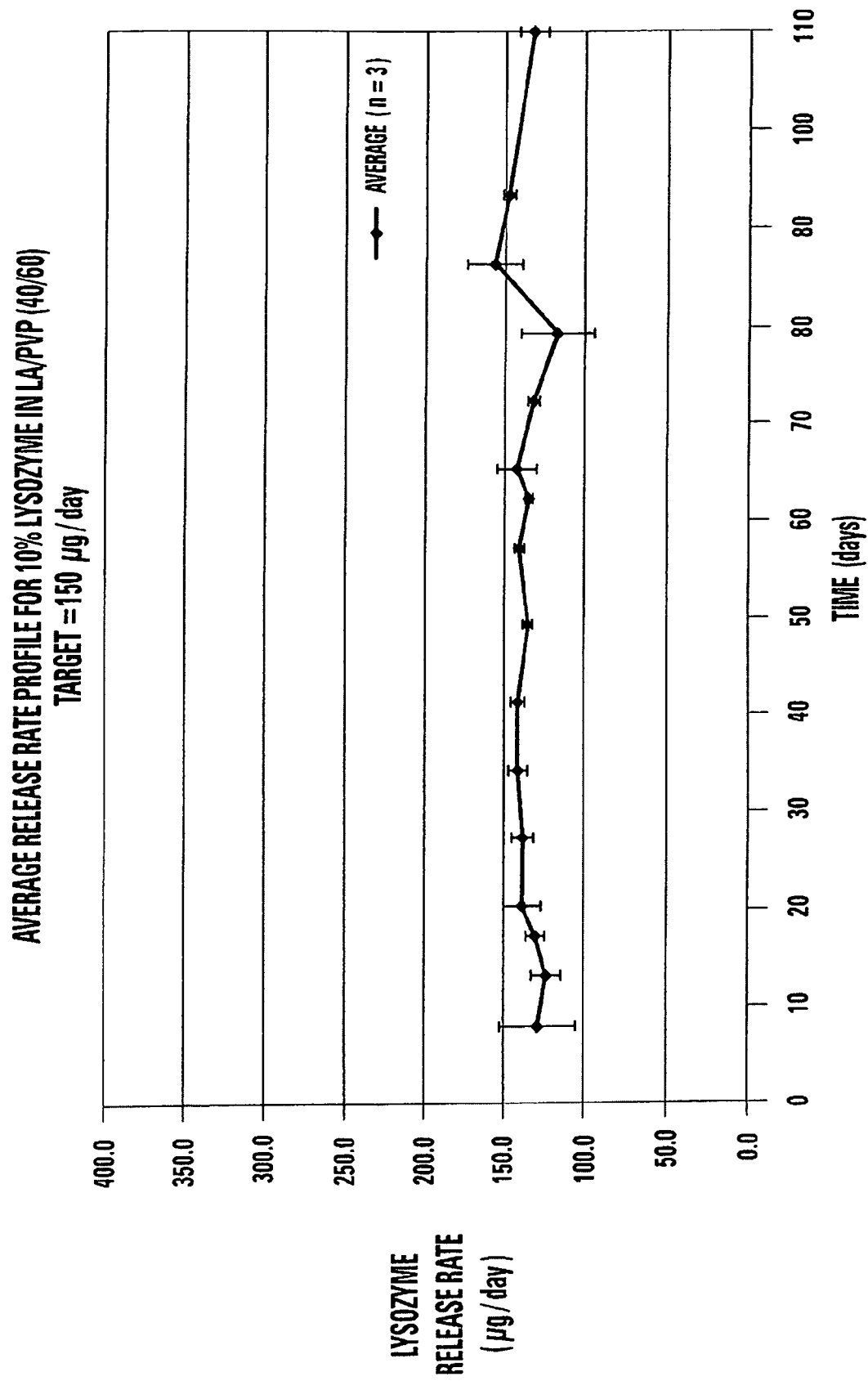
FIG. 5 shows the average release rate (μg/day) of 10% lysozyme in a lauryl alcohol/polyvinylpyrrolidone vehicle.
Figure 6:
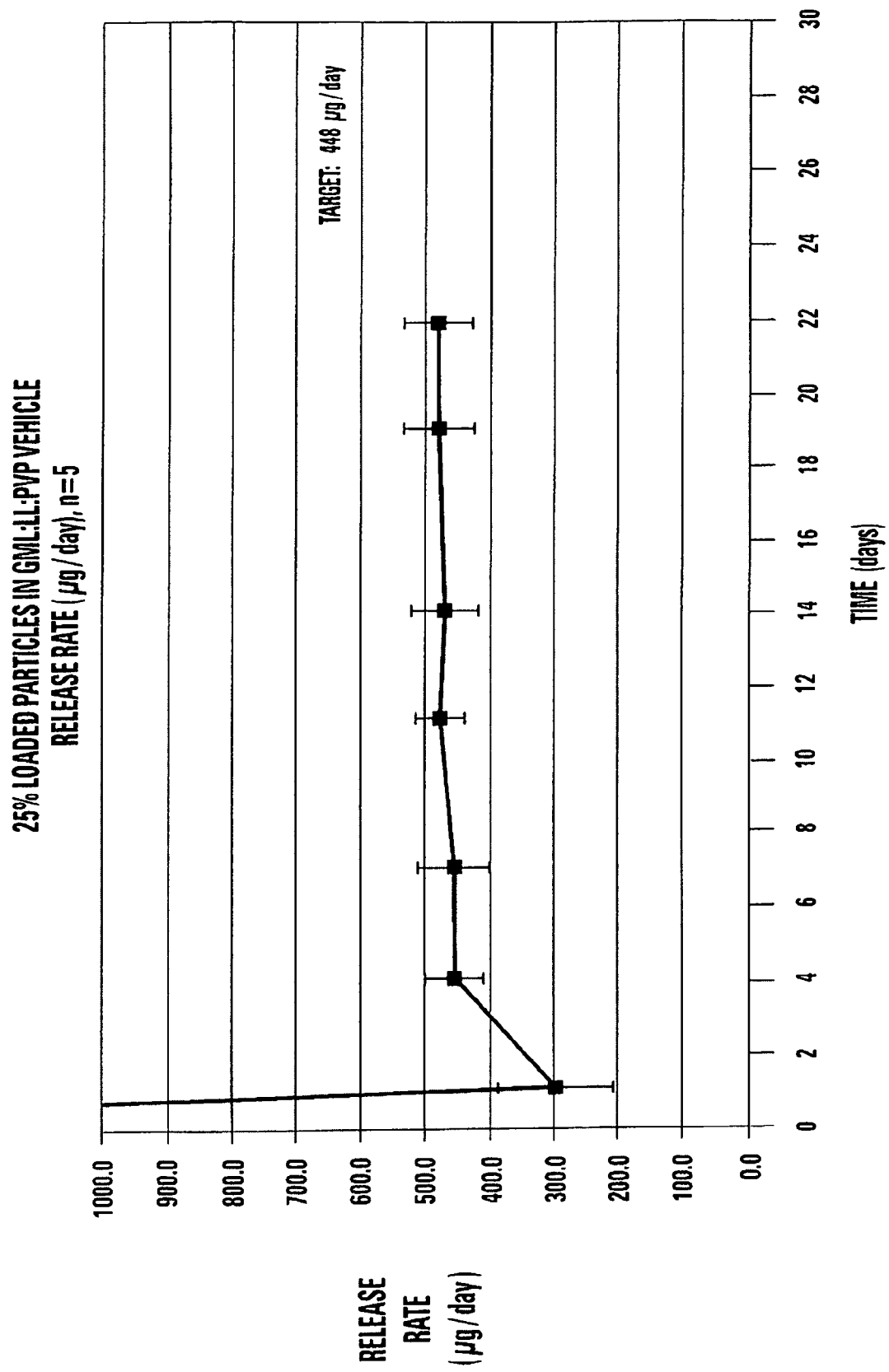
FIG. 6 shows the average release rate ((μg/day) of 25% lysozyme in a glycerol monolaurate/lauryl lactate/polyvinylpyrrolidone vehicle.
Figure 7:
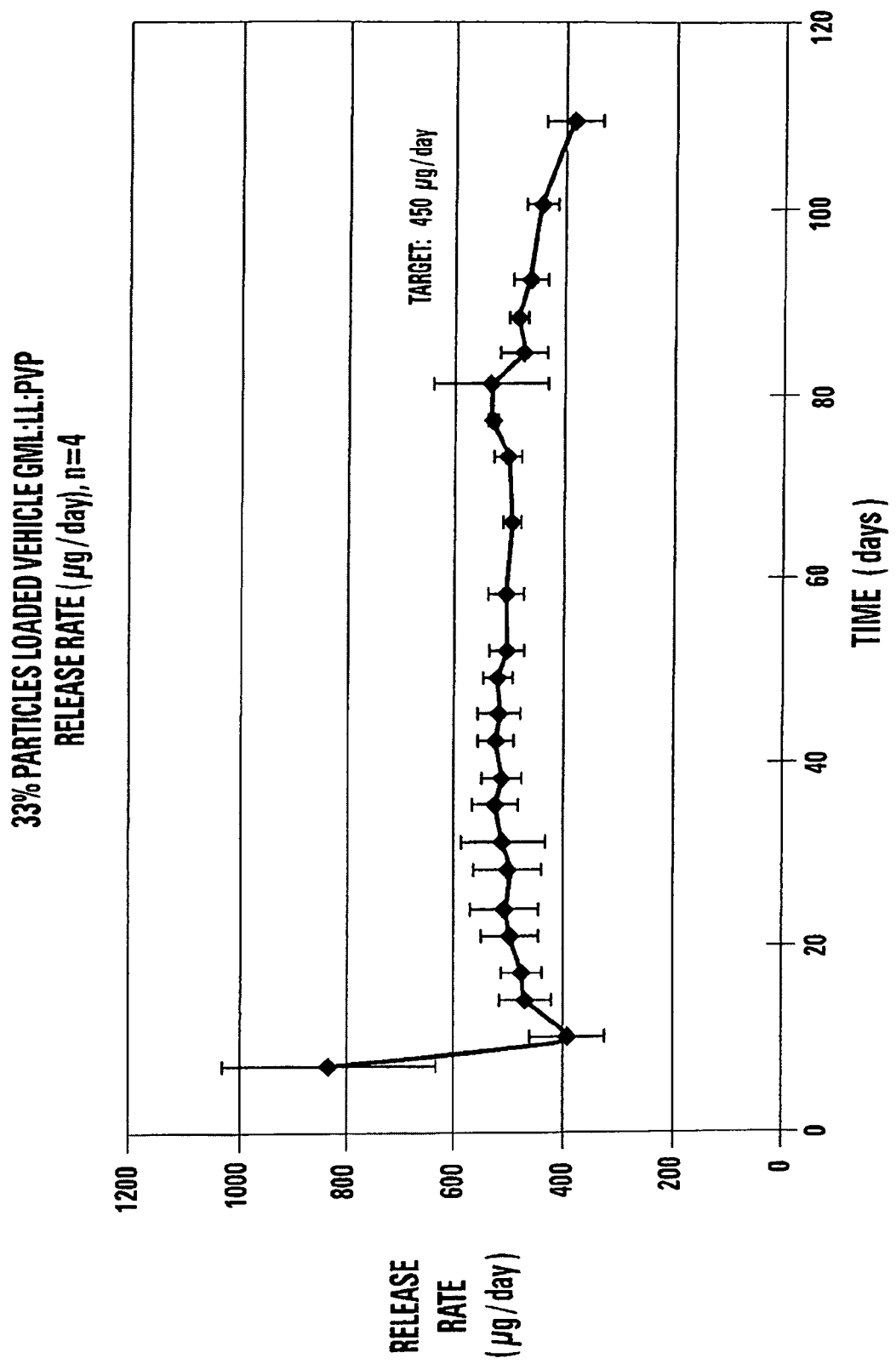
FIG. 7 shows the average release rate ((μg/day) of 33% lysozyme in a glycerol monolaurate/lauryl lactate/polyvinylpyrrolidone vehicle.
Figure 8:
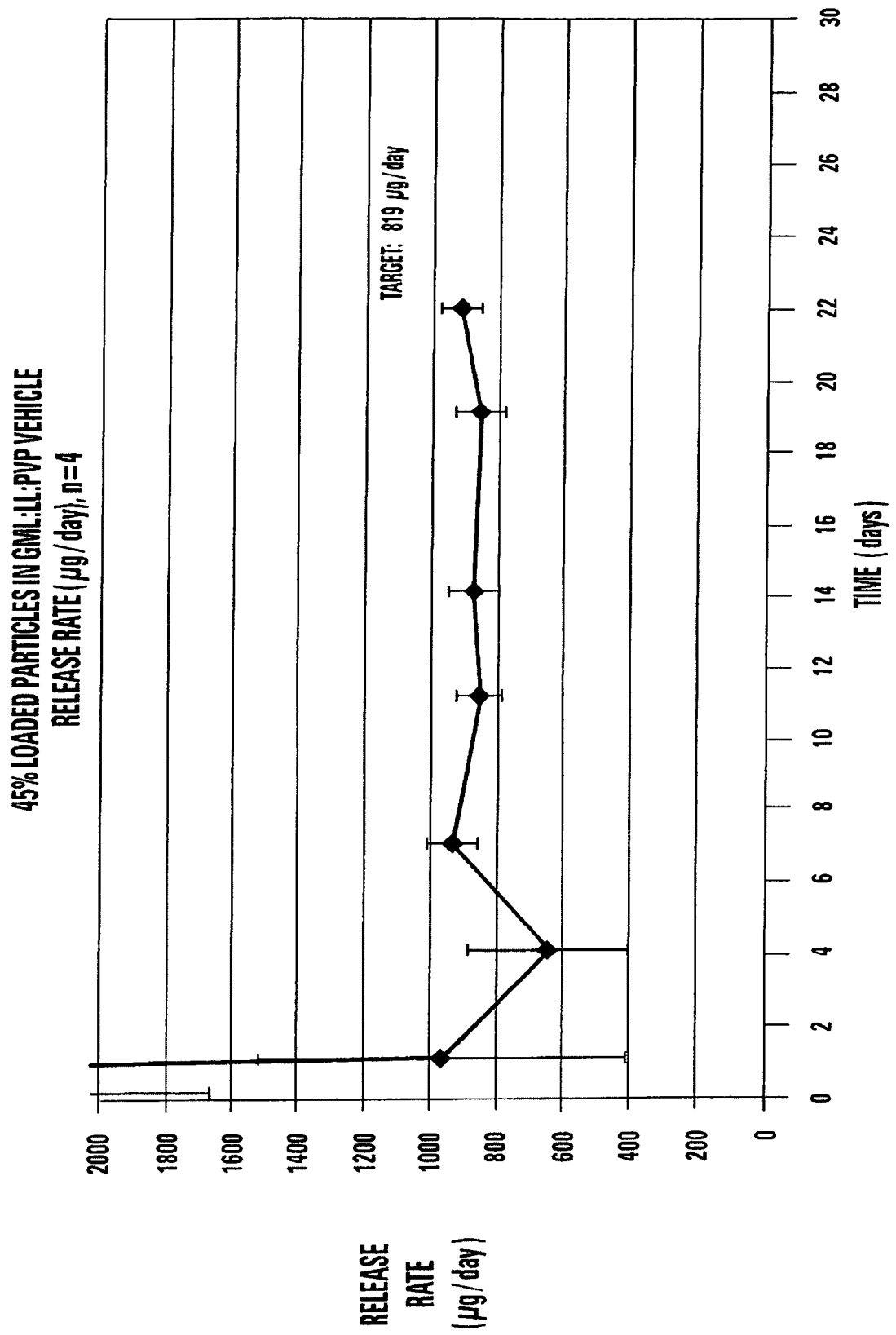
FIG. 8 shows the average release rate ((μg/day) of 45% lysozyme in a glycerol monolaurate/lauryl lactate/polyvinylpyrrolidone vehicle.

It has been unexpectedly found that using a stable non-aqueous single phase biocompatible viscous vehicle increases the stability of the beneficial agent. For example, as seen in FIGS. 1 and 2, human growth hormone (hGH) was found to be stable at 37° C. over 12 weeks in formulations of polyvinylpyrrolidone/PEG; Pluronic; and glycerol monolaurate/lauryl lactate/polyvinylpyrrolidone. FIG. 1 shows stability results using reverse phase HPLC. FIG. 2 shows stability results using size exclusion chromatography.

Generally, stable non-aqueous single phase biocompatible viscous vehicles may be prepared by combining the dry (low moisture content) ingredients in a dry box or under other dry conditions and blending them at elevated temperature, preferably about 40 to about 70° C., to allow them to liquify. The liquid vehicle is allowed to cool to room temperature. Differential scanning calorimetry was used to verify that the vehicle was single phase. The final moisture content of the viscous vehicle was <2%.

Generally, the stable formulations of the present invention may be prepared by combining the vehicle and beneficial agent under dry conditions and blending them under vacuum at elevated temperature, preferably about 40 to about 70° C., to disperse the beneficial agent uniformly throughout the vehicle. The formulation is allowed to cool to room temperature.

It has been found that drying the beneficial agent prior to formulation enhances the stability of the formulation.

Figure 9:
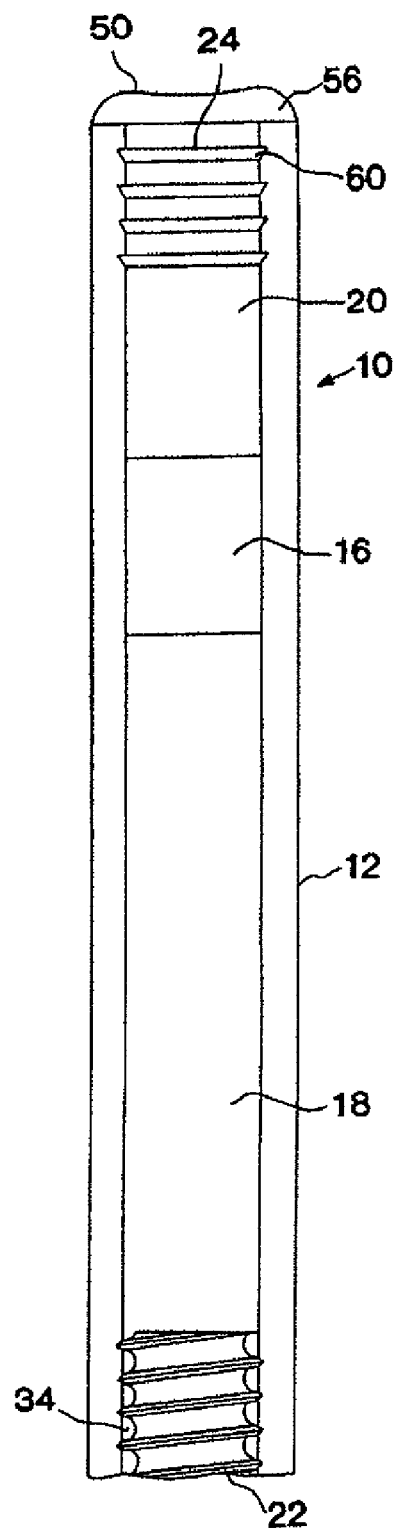
FIG. 9 and FIG. 10 are partial cross-sectional views of two embodiments of the delivery device of the invention.

It has also been found that adding antioxidants, such as tocopherol, ascorbic acid, ascorbyl palmitate, butylated hydroxyanisole, butylated hydroxytoluene, and propyl gallate reduces the formation of degradation products (e.g., unstable chemical intermediates) during sterilization.

Methodology

We have found that stable non-aqueous beneficial agent formulations utilizing viscous vehicles may be prepared by combining the ingredients for the viscous vehicle under dry conditions and blending them at elevated temperature to allow them to liquify and form a single phase. Once a single phase viscous vehicle is formed, the vehicle is allowed to cool to room temperature. Beneficial agent is added with mixing at elevated temperature under vacuum to uniformly disperse it in the viscous vehicle.

We have tested these beneficial agent formulations, for example formulations of hGH, for stability by subjecting them to accelerated aging tests. Results show that these formulations remained stable over extended periods of time.

We have tested beneficial agent formulations, for example human growth hormone and lysozyme, for stability by suspending them in a variety of non-aqueous single phase viscous vehicles prepared according to the present invention, then subjecting them to accelerated aging at elevated temperatures. The stability of the formulations was measured. Results of these studies demonstrate that these formulations were stable at conditions that approximate or exceed storage for one year at 37° C.

We have also tested beneficial agent formulations prepared as described herein for stability after 2.5 megarads gamma irradiation. Results show that these formulations remained chemically and physically stable after such irradiation.

Methods

The following methods were used to perform the studies in the Examples that follow.

1. Preparing Protein Powders

Human Growth Hormone (Obtained for Example, from BresaGen Limited, Adelaide, Australia)

The active agent was reconstituted in deionized water. The solution containing the active agent was buffer exchanged using an Amicon Diaflo® Ultrafiltration membrane (molecular weight cut-off 10,000).

The diafiltrated active agent solution was spray dried using a Yamato mini-spray dryer. Powder was collected in a collection vessel through a cyclone trap. All handling of the spray dried powder took place in a dry box evacuated with nitrogen. The generated powder was analyzed for particle size and distribution, moisture content, protein content and stability by size exclusion and reverse-phase chromatography.

It is known that the conformation of some proteins can be stabilized by the addition of a sugar (such as sucrose or mannitol) or a polyol (such as ethylene glycol, glycerol, glucose, and dextran.)

2. Preparation of Viscous Vehicles

We have found that stable single phase biocompatible viscous vehicles may be prepared by combining the ingredients and blending them at elevated temperatures to allow them to liquify and form a single phase. A differential scanning calorimetry scan showed one peak, indicative of a single phase. The mixing was completed under vacuum to remove trapped air bubbles produced from the powders. The mixer was a dual helix blade mixer (D.I.T.) which runs at a speed around 40 rpm. Higher speeds can be used but are not required.

If a three component viscous vehicle is prepared, the solvent portion of the vehicle was added to the heated bowl of the mixer first, followed by the surfactant. The polymer was added last, and the ingredients were mixed until a solution (single phase) resulted. Vacuum was applied during mixing to remove air bubbles. The solution was dispensed from the bowl while at elevated temperature, and allowed to cool to room temperature. On cooling the vehicle exhibited increased viscosity. Two and single component gels were made using the same process.

3. Preparation of Beneficial Agent Formulations

To prepare the formulation, the single phase viscous vehicle was heated and then blended under vacuum with a weighed amount of beneficial agent. The beneficial agent and the single phase viscous vehicle were blended in the same manner as the vehicle was prepared, using a dual helix blade mixer (or other similar mixer). Mixing speed was between 40 and 120 rpm for approximately 15 minutes or until a uniform dispersion was attained. The resulting mixture was removed from the mixer, sealed in a dry container, and allowed to cool to room temperature.

4. Preparation of Reservoirs

FIG. 9 shows one embodiment of the device according to the invention. In FIG. 9 a fluid-imbibing system 10 is shown that comprises an impermeable reservoir 12. The reservoir 12 is divided into two chambers by a piston 16. The first chamber 18 is adapted to contain an active agent and the second chamber 20 is adapted to contain a fluid-imbibing agent. A back-diffusion regulating outlet 22 is inserted into the open end of the first compartment 18 and a water-swellable semipermeable plug 24 is inserted into the open end of the second chamber 20. In FIG. 9, the back-diffusion regulating outlet 22 is shown as a male threaded member in a mating relationship with the smooth interior surface of the reservoir 12 thereby forming therebetween helical flow path 34. The pitch (x), the amplitude (y), and the cross-sectional area and shape of the helical path 34 formed between the mating surfaces of the back-diffusion regulating outlet 22 and the reservoir 12 as shown in FIG. 11 are factors that affect both the efficiency of path 34 preventing back-diffusion of external fluid into the formulation in chamber 18 and the back pressure in the device. The geometry of outlet 22 prevents water diffusion into the reservoir. In general, it is desired that these characteristics be selected so that the length of the helical flow path 34 and the velocity of flow of active agent therethrough is sufficient to prevent back-diffusion of external fluid through the flow path 34 without significantly increasing the back pressure, so that, following start-up, the release rate of the active agent is governed by the osmotic pumping rate.

FIG. 10 is a second embodiment of the device of the invention with a reservoir 12, piston 16 and plug 26. In this embodiment, the flow path 36 is formed between a threaded back-diffusion regulating outlet 40 and threads 38 formed on the interior surface of the reservoir 12. The amplitudes of the threaded portions of the back-diffusion regulating outlet 40 and reservoir 12 are different so that a flow path 36 is formed between the reservoir 12 and the back-diffusion regulating outlet 40. The water-swellable semipermeable plugs 24 and 26 shown in FIGS. 9 and 10 respectively are inserted into the reservoir such that the reservoir wall concentrically surrounds and protects the plug.

In FIG. 9, the top portion 50 of the plug 24 is exposed to the environment of use and may form a flanged end cap portion 56 overlaying the end of reservoir 12. The semipermeable plug 24 is resiliently engaged with the interior surface of the reservoir 12 and in FIG. 9 is shown to have ridges 60 that serve to frictionally engage the semipermeable plug 24 with the interior of reservoir 12. In addition, the ridges 60 serve to produce redundant circumferential seals that function before the semipermeable plug 24 expands due to hydration. The clearance between ridges 60 and the interior surface of the reservoir 12 prevents hydration swelling from exerting stresses on the reservoir 12 that can result in tensile failure of the reservoir 12 or compression or shear failure of the plug 24.

Figure 10:
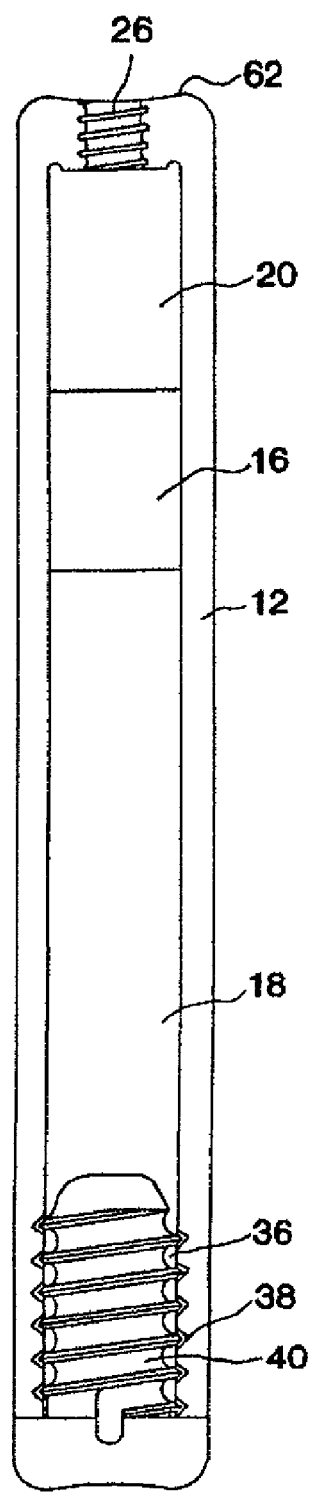
Figure 11:
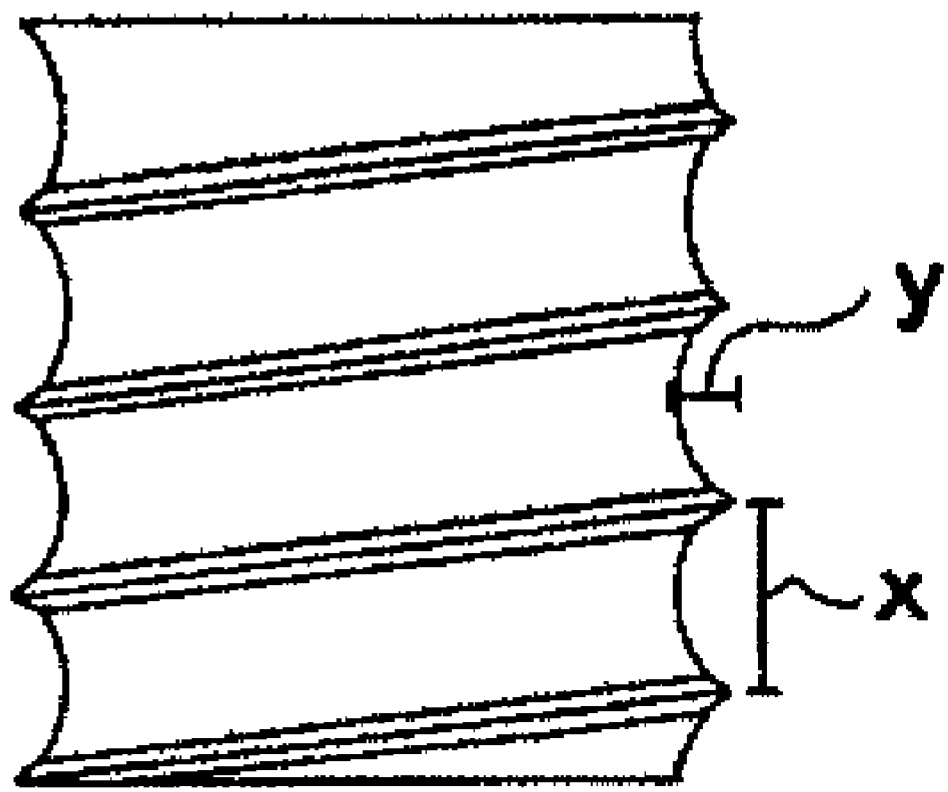
FIG. 11 is an enlarged cross-sectional view of the back-diffusion regulating outlet of FIG. 9.

FIG. 10 shows a second embodiment of the semipermeable plug 26 where the plug is injection molded into the top portion of the reservoir and where the top of the semipermeable plug 26 is flush with the top 62 of the reservoir 12. In this embodiment, the diameter of the plug is substantially less than the diameter of the reservoir 12. In both embodiments the plugs 24 and 26 will swell upon exposure to the fluid in body cavity forming an even tighter seal with the reservoir 12.

An example of assembly of a delivery device is as follows. The piston and inner diameter of the reservoir are lightly lubricated with silicon medical fluid. The piston 16 is inserted into the open end of chamber 20. Two osmotic engine tablets (40 mg each) are then inserted on top of piston 16. After insertion, the osmotic engine is flush with the end of the reservoir. The membrane plug 24 is inserted by lining up the plug with the reservoir and pushing gently until the plug is fully engaged in the reservoir. Active agent is loaded into a syringe which is then used to fill chamber 18 from its open end by injecting the material into the open tube until the formulation is ~3 mm from the end. The filled reservoir is centrifuged (outlet end "up") to remove any air bubbles that are trapped in the formulation during filling. The outlet 22 is screwed into the open end of the reservoir until completely engaged. As the outlet is screwed in, excess formulation exits out of the orifice ensuring a uniform fill.

The reservoirs of implantable drug delivery devices (as disclosed in U.S. patent application Ser. No. 08/595,761, filed 2 Feb. 1996 (which was converted by petition to U.S. Provisional Patent Application Ser. No. 60/122,056 on 21 Jan. 1997), incorporated herein by reference) were filled with the appropriate hGH formulation. The formulation was filled into titanium reservoirs with a polymer plug blocking each end. The filled reservoir was then sealed in a polyfoil bag and placed in a stability testing oven.

It should be noted that the formulations in the reservoirs of these devices are completely isolated from the outside environment.

5. Reverse Phase-HPLC (RP-HPLC)

All stability samples of hGH were assayed for protein content and chemical stability by reverse phase chromatography (RP-HPLC). Analyses were performed on a Hewlett Packard HP-1090 system with a refrigerated autosampler (4° C.). The chromatographic conditions used are listed below.

TABLE 1

| RP-HPLC Chromatographic Conditions | |
|---|---|
| Description | Parameter |
| Column | J.T. Baker-C18, 4.6 × 250 mm |
| Flow Rate | 1.0 mL/min |
| Detection | 214 nm |
| Mobile Phase | A: 0.1% TFA in water |
| | B: 0.1% TFA in acetonitrile |
| | time   %A   %B |
| Gradient | 0   65   35 |
| | 5   50   50 |
| | 45   35   65 |
| | 50   30   70 |
| | 55   65   35 |

An hGH reference standard solution was prepared and its protein content calculated from the absorbance measurement at 280 nm. Three dilutions of this solution, representing 80%, 100%, and 120% of the expected concentration of hGH in the samples were run in duplicate at the beginning and the end of each run and used to calculate total protein content of the samples.

6. Size Exclusion Chromatography (SEC)

All stability samples of hGH were assayed for protein content and high molecular weight degradation products by size exclusion chromatography. Analyses were performed on a Hewlett Packard HP-1090 system with a refrigerated autosampler (4° C.). The chromatographic conditions used are listed below

TABLE 2

| SEC Chromatographic Conditions | |
|---|---|
| Description | Parameter |
| Column | TSK-2000SWXL |
| Flow Rate | 0.5 ml/min |
| Detection | 214 nm |
| Mobile Phase | 25 mM sodium phosphate, 100 mM sodium chloride, pH 7.0 |

A hGH reference standard solution was prepared and its protein content calculated from the absorbance measurement at 280 nm. Three dilutions of this solution, representing 80%, 100%, and 120% of the expected concentration of hGH in the samples were run in duplicate at the beginning and the end of each run and used to calculate total protein content of the samples. The amount of high molecular weight degradation products was calculated by area normalization.

The following examples are offered to illustrate this invention and are not meant to be construed in any way as limiting the scope of this invention.

EXAMPLE 1

Preparation of Non-aqueous Single Phase Viscous Vehicles

The non-aqueous single phase viscous vehicles can be prepared as follows and shown in the below table A. Glycerol monolaurate (Danisco Ingredients, New Century, Kans.) (25 g) was dissolved in lauryl lactate (ISP Van Dyk Inc., Belleville, N.J.) (35 g) at 65° C. Polyvinylpyrrolidone C30 (BASF, Mount Olive, N.J.) (40 g) was added and the mixture blended at about 40 rpm in a dual helix blade mixer (D.I.T.) until a single phase was achieved. Trapped air bubbles were removed by applying vacuum to the mixing chamber. The single phase vehicle was dispensed from the mixer, and allowed to cool to room temperature.

B. Glycerol monolaurate (Danisco Ingredients, New Century, Kans.) (25 g) was dissolved in lauryl lactate (ISP Van Dyk Inc., Belleville, N.J.) (35 g) at 65° C. Polyvinylpyrrolidone C17 (BASF, Mount Olive, N.J.) (40 g) was added and the mixture blended at about 40 rpm in a dual helix blade mixer (D.I.T.) until a single phase was achieved. Trapped air bubbles were removed by applying vacuum to the mixing chamber. The single phase vehicle was dispensed from the mixer, and allowed to cool to room temperature.

C. Polyvinylpyrrolidone C30 (BASF, Mount Olive, N.J.) (50 g) was dissolved in polyethylene glycol 400 (Union Carbide) (50 g) at approximately 65° C., until a single phase solution was formed. The single phase vehicle was dispensed from the mixer, and allowed to cool to room temperature.

D. Polyvinylpyrrolidone C17 (BASF, Mount Olive, N.J.) (50 g) was dissolved in polyethylene glycol 400 (Union Carbide) (50 g) at approximately 65° C. until a single phase solution was formed. The single phase vehicle was dispensed from the mixer, and allowed to cool to room temperature.

E. Polyvinylpyrrolidone C17 (BASF, Mount Olive, N.J.) (50 g) was dissolved in castor oil (Spectrum, Gardena, Calif.) (50 g) at approximately 65° C. until a single phase solution was formed. The single phase vehicle was dispensed from the mixer, and allowed to cool to room temperature.

F. Polyvinylpyrrolidone C17 (BASF, Mount Olive, N.J.) (50 g) was dissolved in octanoic acid (Spectrum, Gardena, Calif.) at approximately 65° C. until a single phase solution was formed. The single phase vehicle was dispensed from the mixer, and allowed to cool to room temperature.

G. Polyvinylpyrrolidone C17 (BASF, Mount Olive, N.J.) (50 g) was dissolved in oleic acid (Spectrum, Gardena, Calif.) at approximately 65° C. until a single phase solution was formed. The single phase vehicle was dispensed from the mixer, and allowed to cool to room temperature.

H. Polyvinylpyrrolidone C17 (BASF, Mount Olive, N.J.) (35%) was dissolved in glycerin (Baker, N.J.) (65%) at approximately 65° C. until a single phase solution was formed. The single phase vehicle was dispensed from the mixer, and allowed to cool to room temperature.

I. Cremophor EL (ethoxylated castor oil) (BASF, Mount Olive, N.J.) (5%) was dissolved in castor oil (Spectrum, Gardena, Calif.) (70%), and polyvinylpyrrolidone C17 (BASF, Mount Olive, N.J.) (25%) was added and dissolved by mixing at approximately 40 rpm to form a single phase vehicle. The single phase vehicle was dispensed from the mixer, and allowed to cool to room temperature.

J. Pluronic 105 (BASF, Mount Olive, N.J.) was heated to approximately 65° C. with mixing until melted. The single phase vehicle was dispensed from the mixer, and allowed to cool to room temperature.

K. Pluronic F68 (BASF, Sigma) 10% w/w and butylhydroxytoluene (Spectrum) 1% w/w were dissolved in 49% w/w propylene carbonate (Aldrich) by mixing under vacuum at 60° C. until the materials dissolved. The vacuum was released, and the resulting liquid was added to 40% w/w poly lactic acid [poly(D,L-lactide), Resomer R207, Boehringer Ingelheim]. All components were mixed by hand at 60° C. using a spatula until the poly lactic acid was dissolved to form a single phase vehicle. The single phase vehicle was moved to a vacuum chamber to remove remaining air bubbles and allowed to cool to room temperature.

L. Myristyl lactate (Ceraphyl 50, ISP Van Dyk) 20% w/w was dissolved in 25% w/w lauryl alcohol (Sigma) under vacuum at 60° C. until the material dissolved. The vacuum was released, and the resulting liquid was added to a mixing bowl. 55% w/w Polyvinylpyrrolidone (BASF, 17 pf) was added on top and the contents of the bowl were mixed at 40 rpm at 60° C. under vacuum until all components were miscible and formed a single phase vehicle. Vacuum was applied until air bubbles were removed from the single phase vehicle.

TABLE 3

Component Ratios

| Polymer | Component Surfactant | Solvent | Ratio | Viscosity at Low Shear Rate (Poise) |
|---|---|---|---|---|
| PVP | GML | LL | 53:5:42 | 25,000 |
| PVP | GML | LL | 55:10:35 | 50,000 |
| PVP | GML | LL | 50:15:35 | 7,000 |
| PVP | — | LA | 60:40 | |
| PVP | Ceraphyl 50 | LA | 60:10:30 | |
| PVP | — | oleic acid | 50:50 | 30,000 |
| PVP | — | octanoic acid | 55:45 | 7.000 |
| PVP | polysorbate 80 | — | 50:50 | |
| PVP | — | PEG 400 | 50:50 | |
| PVP | caster oil | — | 50:50 | |
| — | Pluronic 105 | — | 100 | 1,000,000 |
| PVP | — | glycerin | 50:50 | 5,000 |
| PLA | F68 | PC | 30:10:60* | |
| PVP (C17) | ML | LA | 50:25:25 | |
| PVP (C17) | polysorbate 80 | LL | 55:40:5 | |

Wherein:
GML = glycerol monolaurate
LL = lauryl lactate
PVP = polyvinylpyrrolidine C30
LA = lauryl alcohol
PEG = polyethyleneglycol 400
F68 = poly(propylene oxide)/poly(ethylene oxide) block copolymer (a Member of the Pluronic family)
PC = propylene carbonate
PLA = poly lactic acid
ML = myristyl lactate
*also contains 1% butylhydroxytoluene

EXAMPLE 2

Preparation of hGH

A. Preparation by Spray Drying

Lyophilized hGH (BresaGen Limited, Adelaide, Australia) was reconstituted in 150 ml of deionized water. This stock solution contained 1050 mg of hGH. Buffer exchange was accomplished using an Amicon Diaflo® Ultrafiltration membrane (molecular weight cut-off 10,000). The ultrafiltration cell was connected to an auxiliary reservoir containing 5 mM phosphate buffer (pH 7). The cell's fluid volume, as well as the hGH concentration, remained constant as excipients were replaced by phosphate buffer.

The diafiltrated protein solution (protein concentration in the solution approximately 2%) was spray dried using a Yamato mini-spray dryer. Settings on the spray dryer were as follows: aspiration pressure constantly adjusted to 1.3 kgf/cm$^2$, inlet temperature 120° C., solution flow rate 2.5 (approximately 3 ml/min). Powder was collected in a collection vessel through a cyclone trap. All handling of the spray dried powder took place in a dry box evacuated with nitrogen (% RH: 1-4%). The water content of the suspending vehicles is shown in the below table.

TABLE 4

WATER CONTENT OF SUSPENDING VEHICLES

| Vehicle | Water Content of Vehicle at T 0 % w/w | Water Content of Vehicle in 12 wks. At 37° C. % w/w |
|---|---|---|
| Pluronic 105 | 0.25 | 0.4 |
| GML/LL/PVP | 1.5 | 1.3 |
| PVP/PEG | 2.0 | 2.0 |

Wherein:
GML = glycerol monolaurate
LL = lauryl lactate
PVP = polyvinylpyrrolidine C30
PEG = polyethyleneglycol 400

EXAMPLE 3

Preparation of hGH Formulation

A portion of the single phase viscous vehicle was weighed (9 g) and heated to 60° C. hGH (BresaGen Limited, Adelaide, Australia) (1 g) was added to the vehicle and mixed for 15 minutes. The mixing was completed under vacuum to remove air bubbles added from the powder.

Approximately 10 mg of the spray-dried hGH powder were weighed out (content of hGH in the powder was recalculated based on the determined water and salt content) and mixed with 100 µl of the vehicle at 55-65° C. (3 samples per each vehicle). Special care was taken while mixing powder in the suspending vehicle to achieve maximum particle uniform dispersion in the vehicle. All steps were done in a dry box.

The resulting suspension was dissolved with 10 ml of release rate buffer and analyzed by size exclusion and reverse-phase chromatography. Spray dried hGH powder was used as a control.

TABLE 5

STABILITY OF hGH SUSPENSIONS AT 37° C. AS MEASURED BY SIZE EXCLUSION CHROMATOGRAPHY

| Time Weeks | Spray-dried Powder −80° C. % LS | PVP/PEG 400 suspension % LS | GML/LL/PVP suspension % LS | Pluronic 105 suspension % LS |
|---|---|---|---|---|
| 0 | 96 ± 1 | 88 ± 6 | 92 ± 2 | 87 ± 7 |
| 1 | 99 ± 8 | 81 ± 2 | 94 ± 3 | 93 ± 3 |
| 2 | 99 ± 3 | 83 ± 1 | 97 ± 1 | 94 ± 1 |
| 3 | 97 ± 1 | 84 ± 2 | 95 ± 2 | 95 ± 3 |
| 4 | 95 ± 2 | 82 ± 8 | 94 ± 4 | 93 ± 5 |
| 7 | 95 ± 4 | 76 ± 3 | 93 ± 4 | 88 ± 2 |
| 12 | 97 ± 4 | 79 ± 3 | 97 ± 1 | 95 ± 6 |

Each data point represents the mean ± relative standard deviation of three individual samples taken from three separate vials.

TABLE 6

STABILITY OF hGH SUSPENSIONS at 37° C. AS MEASURED BY REVERSE PHASE CHROMATOGRAPHY

| Time Weeks | Spray-dried Powder −80° C. % LS | PVP/PEG 400 suspension % LS | GML/LL/PVP suspension % LS | Pluronic 105 suspension % LS |
|---|---|---|---|---|
| 0 | 104 ± 1 | 99 ± 3 | 99 ± 2 | 89 ± 7 |
| 1 | 104 ± 8 | 78 ± 2 | 98 ± 3 | 96 ± 6 |
| 2 | 104 ± 4 | 73 ± 3 | 95 ± 1 | 96 ± 1 |
| 3 | 104 ± 2 | 78 ± 4 | 97 ± 3 | 97 ± 4 |
| 4 | 100 ± 2 | 74 ± 10 | 93 ± 4 | 96 ± 4 |
| 7 | 108 ± 5 | 72 ± 4 | 96 ± 2 | 94 ± 2 |
| 9 | 102 ± 3 | 66 ± 3 | 92 ± 3 | 93 ± 2 |
| 12 | 101 ± 2 | 66 ± 1 | 89 ± 2 | 92 ± 5 |

Each data point represents the mean ± relative standard deviation of three individual samples taken from three separate vials.

EXAMPLE 4

Preparation of Reservoirs

Release Rate Profiles

Titanium reservoir systems of implantable drug delivery devices (as disclosed in U.S. patent application Ser. No. 08/595,761, filed 2 Feb. 1996 (which was converted by petition to U.S. Provisional Patent Application Ser. No. 60/122,056 on 21 Jan. 1997), incorporated herein by reference) were each assembled with an osmotic engine, piston, and rate controlling membrane (i.e., a semipermeable plug). The reservoirs were filled with the appropriate amount of viscous vehicle formulation and capped with a flow plug (i.e., a back-diffusion regulating outlet). The systems were placed in a water bath at 37° C., and allowed to release formulation for an extended period of time. Released material was sampled twice per week. Assays for released material were completed using reverse phase HPLC. The resulting concentrations of beneficial agent (i.e., active agent) for each system were converted to released amount per day. The beneficial agent was found to have a zero order release from the implantable drug delivery device. As shown in FIGS. 3 through 8.

EXAMPLE 5

Stability of hGH in Non-aqueous Viscous Vehicle Formulations

Formulations of 10% w/w hGH in vehicle were prepared as described above and placed in vials. The formulations were subjected to accelerated aging by storing them at elevated temperatures and times shown in the below table in a controlled temperature oven.

TABLE 7

| Vehicle | Time (hrs) | Temperature | % LS by SEC | % LS by RP-HPLC |
|---|---|---|---|---|
| Pluronic 105 | 0 | 50° C. | 98 ± 3 | 101 ± 3 |
| Pluronic 105 | 1 | 50° C. | 98 ± 3 | 101 ± 4 |
| Pluronic 105 | 2 | 50° C. | 100 ± 1 | 102 ± 3 |
| Pluronic 105 | 4 | 50° C. | 101 ± 3 | 105 ± 3 |
| GML/LL/PVP | 0 | 65° C. | 99 ± 3 | 101 ± 3 |
| GML/LL/PVP | 1 | 65° C. | 93 ± 6 | 97 ± 6 |
| GML/LL/PVP | 2 | 65° C. | 91 ± 5 | 95 ± 5 |
| GML/LL/PVP | 4 | 65° C. | 95 ± 3 | 98 ± 3 |

Each data point represents the mean ± relative standard deviation of three individual samples taken from three separate vials.

Results, presented in the following table, demonstrate that these formulations were able to maintain the stability of the hGH in each case. In each case, at least 70% hGH was retained.

TABLE 8

RECOVERY OF hGH FROM NONAQUEOUS SUSPENSIONS

| Vehicle | % LS by RP-HPLC | % LS by Size-exclusion HPLC |
|---|---|---|
| PVP/PEG 400 | 99 ± 3% | 88 ± 6% |
| GML/LL/PVP | 99 ± 2% | 92 ± 2% |
| Pluronic 105 | 89 ± 7% | 87 ± 7% |

Each data point represents the mean ± relative standard deviation of three individual samples taken from three separate vials.
% LS or % label strength = (measured protein content ÷ theoretical protein content) × 100%

EXAMPLE 6

A. Preparation by Spray Drying

GLP-1 (Polypeptide Laboratories, Wofenbuttel, Germany) was obtained as an acetate salt and was lyophilized. The lyophilized GLP-1 was dissolved in purified water at 19.9 mg/ml and spray dried using a Yamato mini-spray dryer. The spray drying parameters were: 120° C. inlet temperature, 90° C. outlet temperature, solution flow rate 3.3-5.3 ml/min. Powder was collected in a collection vessel through a cyclone trap. All handling of the spray dried powder took place in a dry box evacuated with nitrogen (% RH: 1-4%).

B. Preparation of GLP-1 Formulation

A portion of the single phase viscous vehicle was weighed and heated to 60° C. GLP-1 (Polypeptide Laboratories, Wolfenbuttel, Germany) was added 27% w/w to the vehicle and mixed for 15 minutes. The mixing was completed under vacuum to remove air bubbles.

The resulting suspension was dissolved in 10 ml of release rate buffer and analyzed by size exclusion and reverse-phase chromatography.

C. Analysis of GLP-1 Formulations

The reverse-phase HPLC method consisted of a C-85 µ, 4.6×250 mm analytical column (Higgins Analytical, Mountain View, Calif.) with detection at 210 nm. A step gradient method from 25% B to 80% B at 1 ml/min was as follows: 0-5 min at 25% B, 5-30 min at 25-50% B, 30-35 min at 50-80% B. Mobile phase A was 0.1% TFA in water and mobile phase B was 0.1% TFA in acetonitrile. The formulations were found to be stable for 6 months.

The size exclusion chromatography method consisted of a Pharmacia FPLC HR 10/30 column at a flow rate of 0.5 ml/min. An isocratic method was employed, where the mobile phase was 100 mM ammonium phosphate, 200 mM sodium chloride, pH 2.0, and peptide was deteted at 210 nm. The formulations were found to be stable for 6 months.

D. Preparation of Reservoirs

Titanium reservoir systems of implantable drug delivery devices (as disclosed in U.S. patent application Ser. No. 08/595,761, filed 2 Feb. 1996 (which was converted by petition to U.S. Provisional Patent Application Ser. No. 60/122,056 on 21 Jan. 1997), incorporated herein by reference) were each assembled with an osmotic engine, piston, and rate controlling membrane (i.e., a semipermeable plug). The reservoirs were filled with the appropriate amount of viscous vehicle formulation and capped with a flow plug (i.e., a back-diffusion regulating outlet). The systems were placed in a water bath at 37° C., and allowed to release formulation for an extended period of time. Released material was sampled twice per week. Assays for released material were completed using reverse phase HPLC. The resulting concentrations of beneficial agent (i.e., active agent) for each system were converted to release amount per day. The beneficial agent was found to have a zero order release from the implantable drug delivery device.

Modification of the above-described modes of carrying out various embodiments of this invention will be apparent to those of skill in the art following the teachings of this invention as set forth herein. The examples described above are not limiting, but are merely exemplary of this invention, the scope of which is defined by the following claims.

The invention claimed is:

1. An implantable drug delivery device, comprising
a reservoir containing a beneficial agent formulation that comprises
a stable non-aqueous single phase biocompatible viscous vehicle, comprising a solvent component and a polymer component, wherein the solvent component is a carboxylic acid ester or lauryl alcohol and the polymer component is polyvinylpyrrolidone; and
a beneficial agent uniformly suspended in the vehicle, wherein the beneficial agent is glucagon-like peptide-1 (GLP-1) or a peptide analog thereof;
said implantable drug delivery device further comprising an osmotic engine, a piston, and a rate controlling membrane.

2. The device of claim 1, wherein the vehicle further comprises a surfactant component, wherein the surfactant is glycerol monolaurate or a polysorbate.

3. The device of claim 1, wherein the formulation further comprises an antioxidant.

4. The device of claim 3, wherein the antioxidant is selected from the group consisting of tocopherol, ascorbic acid, ascorbyl palmitate, butylated hydroxyanisole, butylated hydroxytoluene, and propyl gallate.

5. The device of claim 1, wherein the formulation can be delivered from the implantable drug delivery device such that the exit shear rate of the formulation is between about 1 and $1 \times 10^{-7}$ reciprocal second.

6. The device of claim 1, wherein the formulation is stable at body temperature for extended periods of time.

7. The device of claim 1, wherein the formulation comprises at least about 0.1% (w/w) beneficial agent.

8. The device of claim 1, wherein the formulation comprises at least about 10% (w/w) beneficial agent.

9. The device of claim 1, wherein the formulation is stable at 65° C. for at least about 2 months.

10. The device of claim 1, wherein the formulation is stable at 37° C. for at least about 3 months.

11. The device of claim 1, wherein the formulation is stable at 37° C. for at least about one year.

12. The device of claim 1, wherein the beneficial agent is dried to a low moisture content prior to incorporation in the formulation.

13. The device of claim 1, wherein the carboxylic acid ester is lauryl lactate.

14. The device of claim 2, wherein the ratios of the vehicle components are in the range of about 5% (w/w) to about 60% (w/w) for solvent, about 5% (w/w) to about 40% for surfactant, and about 5% (w/w) to about 60% (w/W) for polymer.

15. The device of claim 1, wherein the flow rate from the implantable device is 0.3 to 100 ul/day.

16. The device claim 1, wherein the beneficial agent is prepared by spray-drying.

17. The device of claim 1, wherein the ratios of the components are in the range of 40:60 to 60:40.

18. An implantable drug delivery device, comprising
a reservoir containing a beneficial agent formulation that comprises
a stable non-aqueous single phase biocompatible viscous vehicle, comprising a solvent component and a polymer component, wherein the solvent component is a carboxylic acid ester or lauryl alcohol and the polymer component is polyvinylpyrrolidone; and a beneficial agent uniformly suspended in the vehicle, wherein the beneficial agent is GLP-1;

said implantable drug delivery device further comprising an osmotic engine, a piston, and a rate controlling membrane.

19. The device claim 18, wherein the beneficial agent is prepared by spray-drying.

20. The device of claim 18, wherein the ratios of the components are in the range of 40:60 to 60:40.

* * * * *

UNITED STATES PATENT AND TRADEMARK OFFICE
CERTIFICATE OF CORRECTION

| | | |
|---|---|---|
| PATENT NO. | : 7,919,109 B2 | Page 1 of 1 |
| APPLICATION NO. | : 12/075435 | |
| DATED | : April 5, 2011 | |
| INVENTOR(S) | : Stephen A. Berry et al. | |

It is certified that error appears in the above-identified patent and that said Letters Patent is hereby corrected as shown below:

Column 18, line 54, claim 14: Delete "40%", insert --40% (w/w)--

Column 18, line 55, claim 14: Delete "60% (w/W)", insert --60% (w/w)--

Column 18, line 58, claim 16: Delete "device", insert --device of--

Column 20, line 1, claim 19: Delete "device", insert --device of--

Signed and Sealed this
Ninth Day of August, 2011

David J. Kappos
*Director of the United States Patent and Trademark Office*